(12) United States Patent
Guo et al.

(10) Patent No.: US 10,386,273 B2
(45) Date of Patent: Aug. 20, 2019

(54) 3D TIME SERIES VECTOR SEDIMENT TRAP

(71) Applicant: Lei Guo, Qingdao (CN)

(72) Inventors: Lei Guo, Qingdao (CN); Yanjun Liu, Qingdao (CN); Shizhen Li, Qingdao (CN)

(73) Assignee: Lei Guo, Qingdao (CN)

( * ) Notice: Subject to any disclaimer, the term of this patent is extended or adjusted under 35 U.S.C. 154(b) by 0 days.

(21) Appl. No.: 16/129,832

(22) Filed: Sep. 13, 2018

(65) Prior Publication Data

US 2019/0086299 A1    Mar. 21, 2019

(30) Foreign Application Priority Data

Sep. 15, 2017   (CN) .......................... 2017 1 0832203

(51) Int. Cl.
| | |
|---|---|
| *G01N 1/20* | (2006.01) |
| *C02F 1/00* | (2006.01) |
| *B01D 21/00* | (2006.01) |
| *B01D 21/24* | (2006.01) |
| *G01N 21/33* | (2006.01) |
| *G01N 21/53* | (2006.01) |

(Continued)

(52) U.S. Cl.
CPC ............ *G01N 1/20* (2013.01); *B01D 21/0012* (2013.01); *B01D 21/2411* (2013.01); *C02F 1/001* (2013.01); *G01N 1/2035* (2013.01); *G01N 21/534* (2013.01); *B01D 21/00* (2013.01); *B01D 35/02* (2013.01); *C02F 2103/08* (2013.01); *C02F 2209/11* (2013.01)

(58) Field of Classification Search
CPC .... G01N 1/20; G01N 21/534; B01D 21/2411; B01D 21/0012; C02F 1/001; C02F 2103/08; C02F 2209/11
See application file for complete search history.

(56) References Cited

U.S. PATENT DOCUMENTS

| | | | |
|---|---|---|---|
| 5,922,094 A * | 7/1999 | Richards .................. | F16T 1/00 137/177 |
| 6,503,390 B1 * | 1/2003 | Gannon .............. | B01D 17/005 210/164 |

(Continued)

FOREIGN PATENT DOCUMENTS

| | | |
|---|---|---|
| CN | 2461855 Y | 11/2001 |
| CN | 201020320 Y | 2/2008 |
| CN | 205138838 U | 4/2016 |

*Primary Examiner* — Mohammad K Islam
(74) *Attorney, Agent, or Firm* — Gokalp Bayramoglu

(57) ABSTRACT

A 3D time series vector sediment trap includes a base disposed with trap pipes which includes water flow pipes and sedimentation pipes. The water flow pipes have a horizontal water inlet at the front end, a vertical downward water outlet at the back end and the water flow pipe is internally provided with a filter screen which tilts towards the water inlet. The filter screen is internally tangential to the water flow pipe, and the sedimentation pipes are vertically fixed underneath the water flow pipes. The top end of the sedimentation pipes have an opening and bottom end thereof is closed. The opening is connected to the water flow pipe and directly faces the filter screen so that materials with a diameter greater than the screen pore diameter are intercepted by the filter screen in the water flow pipe and collected in the sedimentation pipe.

9 Claims, 3 Drawing Sheets

(51) Int. Cl.
*B01D 35/02* (2006.01)
*C02F 103/08* (2006.01)

(56) References Cited

U.S. PATENT DOCUMENTS

| | | | | |
|---|---|---|---|---|
| H2231 H | * | 8/2009 | Teoh | F24S 60/30 126/639 |
| 10,202,285 B1 | * | 2/2019 | Happel | C02F 1/004 |
| 2005/0045556 A1 | * | 3/2005 | Kryzak | A01H 4/001 210/602 |
| 2005/0199551 A1 | * | 9/2005 | Gordon | B01D 63/00 210/650 |
| 2007/0068878 A1 | * | 3/2007 | Stever | B01D 21/0012 210/747.3 |
| 2007/0108056 A1 | * | 5/2007 | Nyberg | B01D 61/44 204/554 |
| 2008/0073277 A1 | * | 3/2008 | Paoluccio | B01D 21/0012 210/691 |
| 2009/0114609 A1 | * | 5/2009 | Miller | B01D 17/0211 210/799 |
| 2011/0168612 A1 | * | 7/2011 | Happel | B01D 21/0012 210/122 |
| 2012/0073782 A1 | * | 3/2012 | Moon | F24D 19/1051 165/11.1 |
| 2012/0284210 A1 | * | 11/2012 | Szydlowski | C02F 1/001 705/500 |
| 2013/0022399 A1 | * | 1/2013 | Pierce, Jr. | E02B 3/06 405/31 |
| 2013/0048576 A1 | * | 2/2013 | Bawden | E03F 5/14 210/767 |
| 2013/0068698 A1 | * | 3/2013 | Eddy | B01D 21/0045 210/723 |
| 2013/0068699 A1 | * | 3/2013 | Hannemann | C02F 1/00 210/747.2 |
| 2014/0262988 A1 | * | 9/2014 | Sistla | C02F 1/001 210/90 |
| 2015/0166383 A1 | * | 6/2015 | Visnja | C02F 1/001 205/752 |
| 2015/0259868 A1 | * | 9/2015 | Pierce, Jr. | E02B 3/06 405/23 |
| 2017/0145677 A1 | * | 5/2017 | Coppola | E03F 5/16 |
| 2018/0201532 A1 | * | 7/2018 | McEncroe | C02F 9/005 |
| 2018/0267205 A1 | * | 9/2018 | Harris | G01V 99/005 |
| 2019/0010071 A1 | * | 1/2019 | Reijer Picozzi | B01D 29/15 |
| 2019/0063023 A1 | * | 2/2019 | Pierce, Jr. | E02B 3/06 |
| 2019/0071321 A1 | * | 3/2019 | Sands | C02F 1/28 |

* cited by examiner

3D TIME SERIES VECTOR SEDIMENT TRAP

CROSS REFERENCE TO RELATED APPLICATIONS

This application is based upon and claims priority to Chinese Patent Application No. 201710832203.0, filed on Sep. 15, 2017, the entire contents of which are incorporated herein by reference.

TECHNICAL FIELD

The present invention relates to marine sediment collecting and trapping equipment, and more specifically, to a time series and vector sediment trap.

BACKGROUND

Sediments at the bottom of the deep sea are of great significance to study the marine ecology and deepen the evaluation of the mining impacts on the environment. Abyssal sediments are formed from marine sedimentation, containing plenty of geological and biological information, so survey of types and distribution, transport and dynamic, soil engineering characteristics, microbial communities and other aspects of abyssal sediments are of significance to assess the abyssal mineral resources and environment and future exploitation of resources. Sediments are traditionally collected by sampling equipment which are released by shipboard geological winches, allowed to go down under the effect of gravity and be in the sea for a certain time, and recovered to the sea level. The whole process is beyond monitoring; besides, the equipment is unwieldy and can only obtain a dozen samples within a large time scale. Bottom sampling by applying abyssal vehicles allows scientists to select sampling areas and quantities through a high-definition lens or observation window and improve the sampling efficiency. However, scientists can neither make their real-time selection at sampling points, nor visually obtain samples in real time. This will result in discontinuous data in scientific research and further cause analysis deviation. Serious deviation will make research pointless and a waste of input for scientific research.

SUMMARY

The present invention is to provide equipment which can collect and trap sediments in any direction of the sea bottom in a real-time and dynamic manner, and to calculate the accurate position of corresponding sediments in the sedimentation pipe which enter a sedimentation pipe at any time. Finally, the dynamic change in the content of sediments in the seawater from different directions and different depths with the time as well as corresponding sediment samples at the moments can be obtained.

The technical solution of the present invention is described below:

The 3D time series vector sediment trap comprises a base disposed with trap pipes which consist of water flow pipes and sedimentation pipes, where the water flow pipes have a horizontal water inlet at the front end, a vertical downward water outlet at the back end and a filter screen inside it which tilts towards the water inlet, and the filter screen is internally tangential to the water flow pipe; and the sedimentation pipes, vertically fixed underneath the water flow pipes, have an open top end and a closed bottom end, where the open end communicates with the water flow pipe and directly faces the filter screen so that materials larger than the screen pore diameter are intercepted by the filter screen in the water flow pipe and collected in the sedimentation pipe.

Further, the sedimentation pipes have a tapered guide surface at the respective openings.

Further, a protection pipe is arranged outside of each of the sedimentation pipes.

Further, a second filter screen is arranged at the water outlet.

Further, shackles are disposed on the base.

Further, clump weights are detachably and evenly disposed on top of the base.

Further, insert needles are evenly disposed on the underside of the base.

Further, the water inlet has a horn-shaped guide mouth at the front end.

Further, a current meter, a turbidity meter and an altimeter are disposed inside the water flow pipe, and the altimeter is exactly opposite to the opening of the sedimentation pipe.

A vector method for calculating sediments at any moment, including the following steps:

(1) The sediment content in the water flow pipe is calculated from the data measured by the turbidity meter and the current meter:

① Assuming that the cross section of the water inlet of the trap pipe is S and that of the sedimentation pipe is S';

② Assuming that the current velocity is $V_{(d,D,t)}$ and the turbidity is $Tur_{(d,D,t)}$, then the total amount of the sediments flowing through the water flow pipe at every moment is:

$$Q_{(d,D,i)} = V_{(d,D,i)} \times S \times Tur_{(d,D,i)} \qquad (1)$$

Where d is the direction, D is the depth and i is any moment in the period of time from 0 to t;

(2) Assuming that all sediments $Q_{(d,D,i)}$ flowing through the water flow pipe at every moment flow into the sedimentation pipe, then the corresponding part of the sediments in the sedimentation pipe is from $H_{i-1}$ to $H_i$. The total amount of the sediments in the sedimentation pipe is given from the total amount of the sediments obtained in Step (1):

$$H_i = \frac{1}{S'} \sum_{j=0}^{i} Q_{(d,D,j)} \qquad (2)$$

$$H_{i-1} = \frac{1}{S'} \sum_{j=0}^{i-1} Q_{(d,D,j)} \qquad (3)$$

(3) Sediment samples of any depth and at any moment in the sedimentation pipe in any direction can be given from the change of the sediment height in the sedimentation pipe measured by the altimeter using Formula (1) in Step (1) as well as Formula (2) and Formula (3) in Step (2) and used for physical and chemical analysis.

The trap according to the present invention can dynamically collect sedimenting particulate materials in the seawater flowing through the water flow pipe as the ocean current flows, and acutely monitors environmental changes at the sea bottom; besides, samples are undisturbed, so sampling results are more accurate and reliable. Meanwhile, the present invention provides a vector method for calculating sediments by which the sediment content in the seawater flowing through the water flow pipe in any direction, at any depth and at any moment can be calculated, thus obtaining the corresponding position of these sediments in the trap.

This makes it possible that targeted samples are taken for physical and chemical analysis and is beneficial for test analysis.

Figure 1:
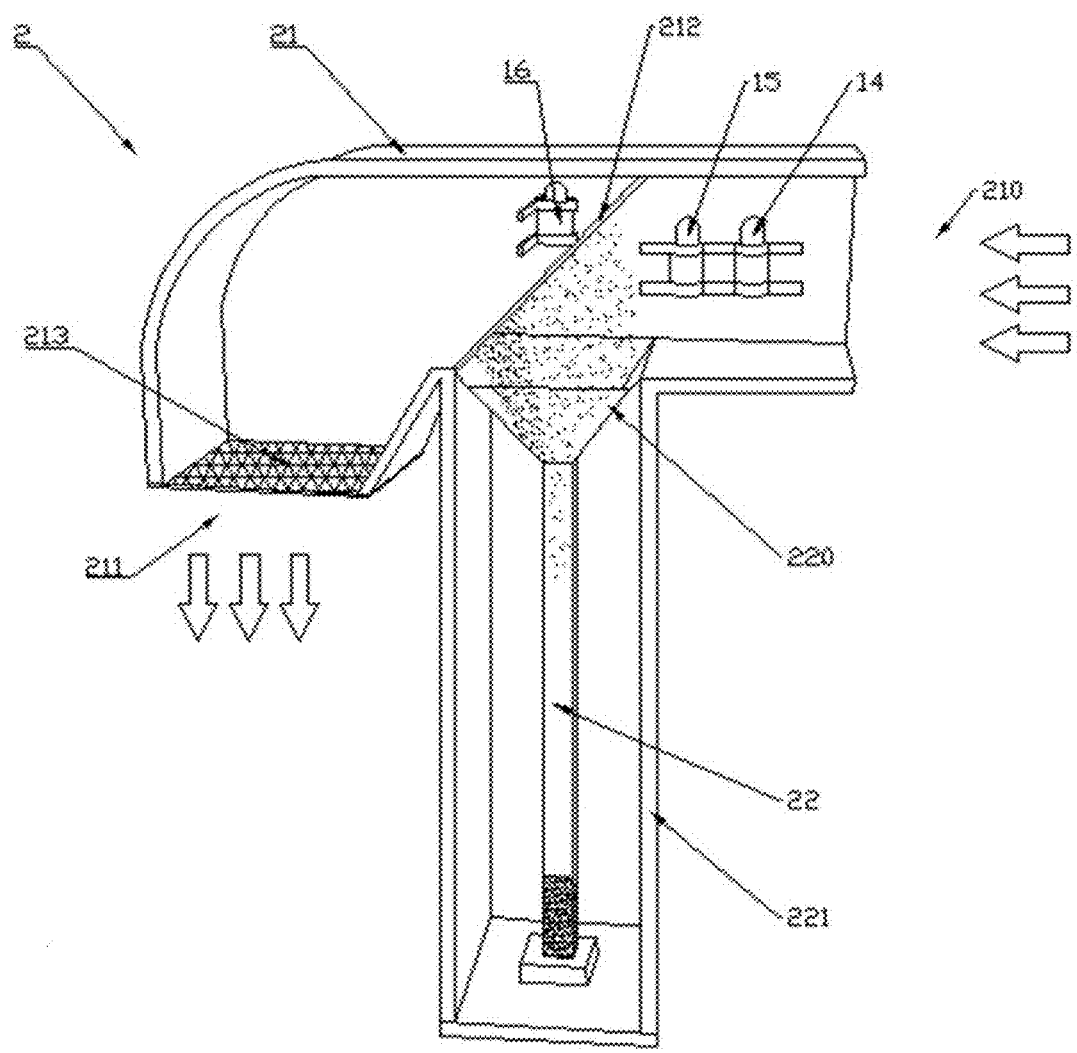
FIG. 1 is Structural Diagram I of the trap according to the present invention.

In the drawings, base 1, clump weight 11, insert needle 12, horn-shaped guide mouth 13, current meter 14, turbidity meter 15, altimeter 16, trap pipe 2, water flow pipe 21, water inlet 210, water outlet 211, filter screen 212, second filter screen 213, sedimentation pipe 22, tapered guide surface 220, and protection pipe 221.

DETAILED DESCRIPTION OF THE EMBODIMENTS

The present invention will be further detailed hereinafter accompanied by the embodiments and drawings.

The 3D time series vector sediment trap comprises a base disposed with trap pipes which consist of water flow pipes and sedimentation pipes, wherein the water flow pipes have a horizontal water inlet at the front end, a vertical downward water outlet at the back end and a filter screen inside it which tilts towards the water inlet, and the filter screen is internally tangential to the water flow pipe; and the sedimentation pipes, vertically fixed underneath the water flow pipes, have an open top end and a closed bottom end, wherein the open end communicates with the water flow pipe and directly faces the filter screen so that materials larger than the screen pore diameter are intercepted by the filter screen in the water flow pipe and collected in the sedimentation pipe.

As shown in FIG. 1, the 3D time series vector sediment trap comprises a base disposed with trap pipes which consist of water flow pipes and sedimentation pipes, wherein the water flow pipes have a horizontal water inlet at the front end, a vertical downward water outlet at the back end and a filter screen inside it which tilts towards the water inlet, and the filter screen is internally tangent to the water flow pipe; and the sedimentation pipes, vertically fixed underneath the water flow pipes, have an open top end and a closed bottom end, wherein the open end communicates with the water flow pipe and directly faces the filter screen so that materials larger than the screen pore diameter are intercepted by the filter screen in the water flow pipe and collected in the sedimentation pipe.

The collection according to the present invention is as below: the seawater flows through the water flow pipe, and when it passes through the filter screen, particulate materials in it are intercepted, fall into the sedimentation pipe and accumulate in it with time until the sedimentation pipe is full. The horizontal water inlet and vertical downward water outlet of the water passage according to the present invention effectively ensure that the direction of the water flow is desired, the sediments in the sedimentation pipes are all from the same direction and the falling of the sediments into the sedimentation will not be disturbed by the water current from the back of the filter screen, so the accuracy rate of data collection is improved.

Figure 2:
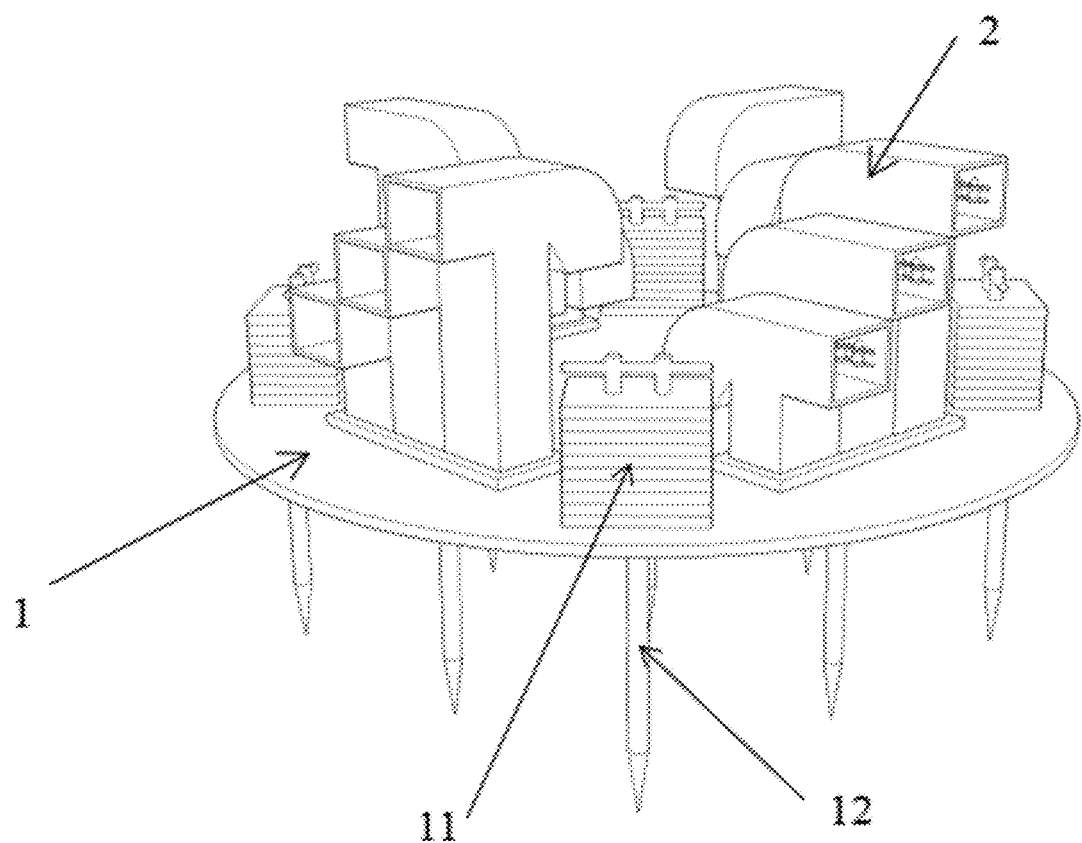
FIG. 2 illustrates the trap featuring multiple directions and multiple depths.

The number of the trap pipes and the inflow direction of the water inlet are not limited in the present invention, but normally set according to data to be collected instead; besides, in order to sample sediments in the seawater at different depths, multiple groups of trap pipes may be disposed at different heights in one direction. As shown in FIG. 2, multiple groups of sediment samples can be taken from different heights in the same direction, so the composition of the sediments in different sea levels can be analyzed, which is beneficial to analysis of the environment at the sea bottom or the influence of environmental changes.

The cross section of the water flow pipes and the sedimentation pipes of the trap is not limited. Where multiple trap pipes of different heights are disposed in the same direction, the cross section of the water flow pipes and the sedimentation pipes are normally set to be square (as shown in FIG. 2), which facilitates arrangement, installation and positioning.

The connection mode between the traps and the base is not limited in the present invention. It may be a permanent connection, which is beneficial to recovery of the traps and the base together. However, sometimes, the base will sediment, so it is difficult to recover the base. In this case, the traps and the base are connected in a mode which can facilitates fixation and detaching, but the connection mode is not limited.

A connection mode facilitating detaching the traps from the base is provided herein, i.e., the bottom end of the outer wall of the traps are made with traverse axle holes, the base is likewise made with fitting axle holes in the same axis with the traverse holes and pins are used to fix the traps onto the base, so that when the base cannot be smoothly recovered for too much sedimentation, the pins are withdrawn and only traps are recovered. The number of the axle holes and fitting axle holes is not limited, but should facilitate fixation and detaching for washing.

The mesh number of the filter screen is not limited in the present invention. Generally, the finer the screen is, the better sampling results are. Fine screens can collect a rich variety of sediments, but a too fine first filter screen will be more easily blocked, so the number is adjusted according to the actual turbidity of sea areas as well as sampling and analysis needs.

Likewise, the inclination angle of the first filter screen relative to the trap mouth is not limited, but preferably acute which can effectively ensure that once intercepted by the first filter screen, sediments quickly and effectively fall into the sedimentation pipe, improving sampling efficiency.

Further, the sedimentation pipes have a tapered guide surface at respective opening. The guide surface is arranged to effectively ensure that sediments smoothly fall into the sedimentation pipe, and increase the dimensions of the filter screen so as to increase the cross section of the water flow pipe and avoid unstable structure due to great difference in dimensions between the water flow pipe and the sedimentation pipe.

Figure 3:
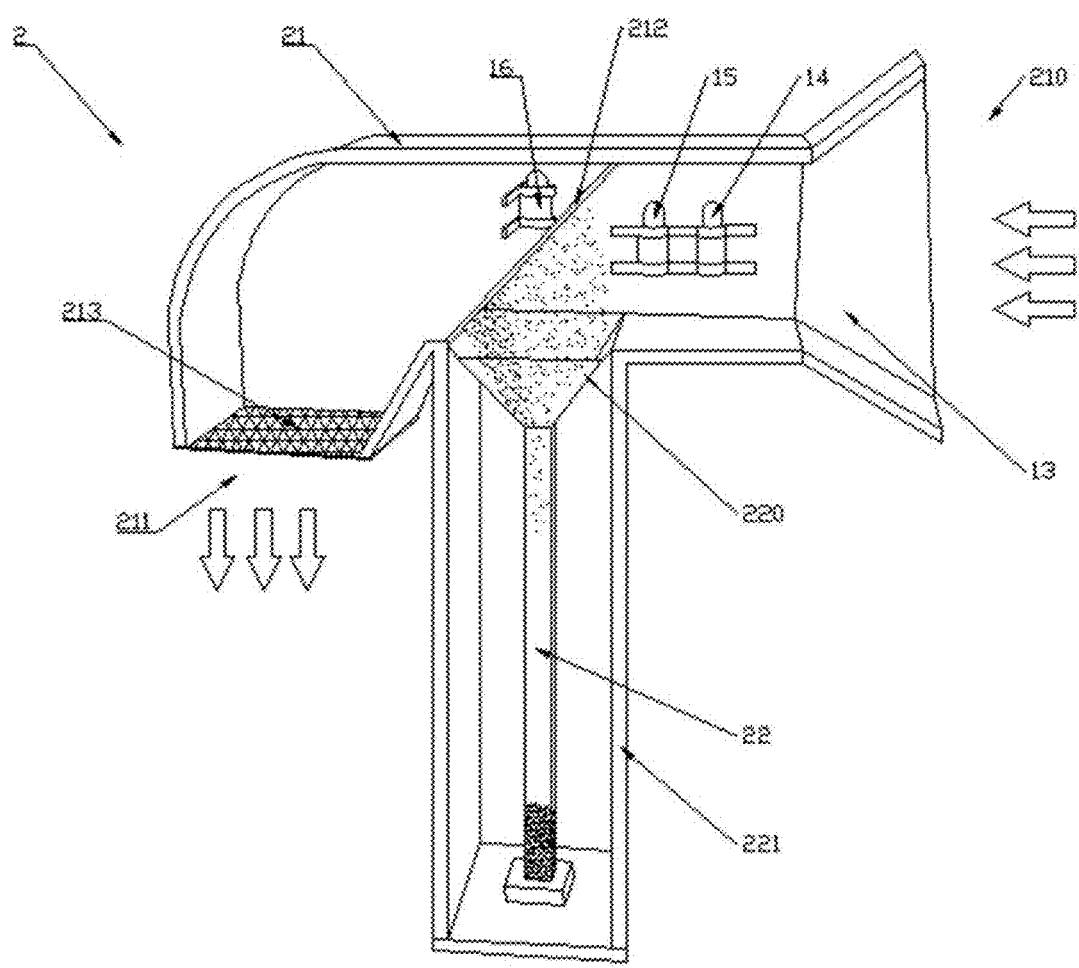
FIG. 3 is Structural Diagram II of the trap according to the present invention.

Further, a protection pipe is arranged outside of each of the sedimentation pipes, which improves the overall stability of the trap. The diameter of the protection pipe may be increased or decreased, and its shape may be the same as or different from that of the sedimentation pipe but not limited. As shown in FIG. 1 and FIG. 3, the water flow pipe is integral with the protection pipe, the sedimentation is arranged inside the protection pipe, and a guide surface is provided between the sedimentation pipe and the water flow pipe.

Further, a second filter screen is arranged at the water outlet. A vertical downward water outlet can effectively prevent the water current in the opposite direction from washing the filter screen, and the second filter screen is to prevent the water current enters the water flow pipe from the opposite direction and then goes into the sedimentation pipe, which further ensure that the sediments in the sedimentation pipe all come from the direction of the water inlet.

In order to facilitate the diving of the base, shackles are disposed on the base. These shackles are separately mounted on the base.

In order to facilitate smooth placing of the base, clump weights are detachably and evenly disposed on top of the base.

The weight, shape and number of the clump weights are not limited and set according to actual use needs. Their even positioning is determined after the positions of the traps are set.

The clump weights may be permanently or detachably connected with the base. Generally speaking, if the seabed is soft and tends to subside, the connection between the base and the clump weights is designed to be detachable so that once the base is properly placed, the clump weights will be recovered to prevent the clump weights from speeding up the subsiding of the base.

The detachable connection mode of the clump weights is not limited but should facilitate fixation and separation. As shown in FIG. 2, a fixation and separation mode of the clump weights and the base is provided. In this embodiment, the top of the base is arranged with vertical positioning posts with a pin hole in respective top end, and the corresponding clump weights have fitting holes for the positioning posts, so that when the clump weights are inserted on the positioning posts and the long clevis pins with head are inserted into the pin holes of the positioning posts, the clump weights are locked on the base. When the base goes down to the predetermined position, the long clevis pins with head are withdrew and the clump weights are separated from the base by means of the rings on the clump weights.

In order to facilitate fixation of the base, insert needles are evenly disposed on the base.

The length of the insert needles is not limited, but should be correspondingly increased or decreased according to the actual conditions of the seabed. The insert needles may be extensible or not extensible but not limited herein. They may be connected with the base by welding, bolts or snap-on but not limited herein.

For example, if there are many stones and sand as well as a small possibility of sedimentation in preliminary exploration, the base can be easily recovered, so detachable connection may be selected for the insert needles and the base. If there is a great possibility that the base sediments into the seabed in preliminary exploration and the recovery is not easily realized, detachable insert needles are pointless, so direct welding may be considered to reduce process and assembly difficulties.

The water inlet has a horn-shaped guide mouth at the front end. The horn-shaped guide mouth can ensure that all water at this height flows into the water flow pipe and all desired sediments fall into the sedimentation pipe.

A current meter, a turbidity meter and an altimeter are disposed inside the water flow pipe, and the altimeter is exactly opposite to the opening of the sedimentation pipe.

The current meter, a turbidity meter and an altimeter are provided to accurately calculate the amount of the sediments entering the sedimentation pipe and the position of the corresponding sediments in the sedimentation pipe at every moment so as to facilitate analysis of samples.

In order to correct the accuracy of sediment collection, a pressure sensor may be arranged at the bottom of the sedimentation tube.

A vector method for calculating sediments at any moment, using a computer processor, including the following steps:

(1) The sediment content in the water flow pipe is calculated from the data measured by the turbidity meter and the current meter:

① Assuming that the cross section of the water inlet of the trap pipe is S and that of the sedimentation pipe is S';

② Assuming that the current velocity is $V_{(d,D,t)}$ and the turbidity is $Tur_{(d,D,t)}$, then the total amount of the sediments flowing through the water flow pipe at every moment is:

$$Q_{(d,D,t)} = V_{(d,D,t)} \times S \times Tur_{(d,D,t)} \qquad (1)$$

Where d is the direction, D is the depth and the i is any moment in the period of time from 0 to t;

(2) Assuming that all sediments $Q_{(d,D,i)}$ flowing through the water flow pipe at every moment flow into the sedimentation pipe, then the corresponding part of the sediments in the sedimentation pipe is from $H_{i-1}$ to $H_i$. The total amount of the sediments in the sedimentation pipe is given from the total amount of the sediments obtained in Step (1):

$$H_i = \frac{1}{S'} \sum_{j=0}^{i} Q_{(d,D,j)} \qquad (2)$$

$$H_{i-1} = \frac{1}{S'} \sum_{j=0}^{i-1} Q_{(d,D,j)} \qquad (3)$$

(3) Sediment samples of any depth and at any moment in the sedimentation pipe in any direction can be given from the change of the sediment height in the sedimentation pipe measured by the altimeter using Formula (1) in Step (1) as well as Formula (2) and Formula (3) in Step (2) and used for physical and chemical analysis.

The collection frequency of the current meter, the turbidity meter and the altimeter is 1 Hz or other value; $d \in \{dE, dS, dW, dN, \ldots\}$, $D \in \{D1, D2, D3, \ldots\}$ and $t \in \{0, 1, 2, \ldots, tN\}$.

The above is just the preferred embodiments of the present invention and not intended to limit the present invention. Those skilled in this profession may make changes or modifications to the technical contents disclosed above and produce equivalent embodiments for application in other fields. Any simple alternation, equivalent change and modification made to the embodiments above based on the technical essence of the present invention and without departure from the technical solution of the present invention are still within the protection scope of the technical solution of the present invention.

What is claimed is:

1. A system of 3D time series vector sediment trap, comprising:

a base, wherein the base is provided with a plurality of trap pipes, and the trap pipes include a water flow pipe and a sedimentation pipe;

wherein, the water flow pipe includes a horizontal water inlet at a front end of the water flow pipe and a vertical downward water outlet at a back end of the water flow pipe, and the water flow pipe is internally provided with a filter screen;

wherein, the filter screen tilts towards the water inlet, and the filter screen is internally tangent to the water flow pipe;

wherein, the sedimentation pipe is vertically fixed underneath the water flow pipe, a top end of the sedimentation pipe has an opening and a bottom end of the sedimentation pipe is closed;

wherein, the opening is connected to the water flow pipe and directly faces the filter screen; the filter screen is configured to intercept materials with a diameter greater than a diameter of a plurality of pores of the filter screen in the water flow pipe and collect the materials in the sedimentation pipe;

wherein, a current meter, a turbidity meter, and an altimeter are disposed inside the water flow pipe, and the altimeter is located exactly opposite to the opening of the sedimentation pipe.

2. The system of 3D time series vector sediment trap of claim 1, wherein the opening of the sedimentation pipe is provided with a tapered guide surface.

3. The system of 3D time series vector sediment trap of claim 2, wherein a protection pipe is arranged outside the sedimentation pipe.

4. The system of 3D time series vector sediment trap of claim 3, wherein a second filter screen is arranged at the vertical downward water outlet of the water flow pipe.

5. The system of 3D time series vector sediment trap of claim 4, wherein the base is provided with a shackle.

6. The system of 3D time series vector sediment trap of claim 5, wherein a plurality of clump weights are detachably and evenly disposed on a top of the base.

7. The system of 3D time series vector sediment trap of claim 6, wherein a plurality of insert needles are evenly disposed on an underside of the base.

8. The system of 3D time series vector sediment trap of claim 7, wherein a front end of the horizontal water inlet of the water flow pipe is provided with a horn-shaped guide mouth.

9. A vector method for calculating sediments, using a computer processor at any moment, wherein the sediments are collected by the system of 3D time series vector sediment trap of claim 1 at a seafloor, comprising:

step a): obtaining a sediment content in a water flow pipe from data measured by a turbidity meter and a current meter;

calculating a total amount of the sediments $Q_{(d,D,t)}$ flowing through the water flow pipe at every moment is expressed by the following formula:

$$Q_{(d,D,i)} = V_{(d,D,i)} \times S \times \text{Tur}_{(d,D,i)} \quad (1)$$

wherein, a cross section of a water inlet of a trap pipe is S, a sedimentation pipe is S', a current velocity is $V_{(d,D,t)}$ and a turbidity is $\text{Tur}_{(d,D,t)}$, wherein, d refers a direction, D refers a depth and i refers any moment in a period of time from 0 to t;

step b): calculating a total amount of the sediments in the sedimentation pipe according to the total amount of the sediments $Q_{(d,D,t)}$ flowing through the water flow pipe at every moment obtained in step a), wherein the total amount of the sediments in the sedimentation pipe is expressed by the following formulas:

$$H_i = \frac{1}{S'} \sum_{j=0}^{i} Q_{(d,D,j)} \quad (2)$$

$$H_{i-1} = \frac{1}{S'} \sum_{j=0}^{i-1} Q_{(d,D,j)} \quad (3)$$

wherein, $Q_{(d,D,i)}$ is the total amount of sediments flowing through the water flow pipe at any moment flow into the sedimentation pipe and a corresponding part of the sediments in the sedimentation pipe is from $H_{i-1}$ to $H_i$, and step c): obtaining a sediment sample of any depth and at any moment in the sedimentation pipe in any direction according to a change of a sediment height in the sedimentation pipe measured by an altimeter using formula (1) in step a) as well as formula (2) and formula (3) in step b) for a physical and chemical analysis.

\* \* \* \* \*